(12) United States Patent
Duerr et al.

(10) Patent No.: US 10,856,837 B2
(45) Date of Patent: Dec. 8, 2020

(54) MICRO-MECHANICAL ADJUSTMENT SYSTEM FOR PIEZOELECTRIC TRANSDUCERS

(71) Applicant: Robert Bosch GmbH, Stuttgart (DE)

(72) Inventors: Andre Duerr, Achstetten (DE); Thomas Rocznik, Mountain View, CA (US); Christian Peters, Mountain View, CA (US); Jochen Stehle, Palo Alto, CA (US)

(73) Assignee: Robert Bosch GmbH, Stuttgart (DE)

( * ) Notice: Subject to any disclaimer, the term of this patent is extended or adjusted under 35 U.S.C. 154(b) by 661 days.

(21) Appl. No.: 15/283,222

(22) Filed: Sep. 30, 2016

(65) Prior Publication Data
US 2018/0092623 A1  Apr. 5, 2018

(51) Int. Cl.
| | | |
|---|---|---|
| *A61B 8/06* | (2006.01) | |
| *A61B 8/00* | (2006.01) | |
| *A61B 8/04* | (2006.01) | |
| *A61B 8/08* | (2006.01) | |

(52) U.S. Cl.
CPC ............... *A61B 8/06* (2013.01); *A61B 8/04* (2013.01); *A61B 8/42* (2013.01); *A61B 8/4254* (2013.01); *A61B 8/4483* (2013.01); *A61B 8/46* (2013.01); *A61B 8/488* (2013.01); *A61B 8/54* (2013.01); *A61B 8/0891* (2013.01); *A61B 8/4281* (2013.01); *A61B 8/4488* (2013.01); *A61B 8/5207* (2013.01)

(58) Field of Classification Search
None
See application file for complete search history.

(56) References Cited

U.S. PATENT DOCUMENTS

| | | | | |
|---|---|---|---|---|
| 5,647,367 A | * | 7/1997 | Lum | A61B 8/12 600/463 |
| 5,701,901 A | * | 12/1997 | Lum | A61B 8/12 600/462 |
| 5,779,643 A | * | 7/1998 | Lum | A61B 8/12 29/25.35 |
| 9,837,935 B2 | * | 12/2017 | Johnson | B81B 3/0086 |
| 2007/0229204 A1 | * | 10/2007 | Ogikubo | G02B 26/0841 335/220 |

(Continued)

FOREIGN PATENT DOCUMENTS

| | | | | |
|---|---|---|---|---|
| EP | 2514365 A1 | * | 10/2012 | .......... A61B 8/0858 |
| EP | 2514365 A1 | | 10/2012 | |
| WO | 2015087218 A1 | | 6/2015 | |

*Primary Examiner* — Patricia J Park
*Assistant Examiner* — Younhee Choi
(74) *Attorney, Agent, or Firm* — Maginot, Moore & Beck LLP

(57) ABSTRACT

A system for detecting blood velocity within a blood vessel includes a transducer array including a plurality of transducers. Each of the transducers includes a carrier substrate, at least one spacer extending upwardly from the substrate, a transducer element attached to the spacer such that the piezoelectric transducer is spaced apart from the substrate, and setting electrodes positioned on the upper surface of the substrate under the piezoelectric transducer. The system also includes a tilt control system that is configured to apply a bias voltage to the setting electrodes which causes the transducer element to pivot about a pivot axis between a first tilted position and a second tilted position.

15 Claims, 11 Drawing Sheets

(56) References Cited

U.S. PATENT DOCUMENTS

2009/0301200 A1* 12/2009 Tanaka .................. B06B 1/0292
73/603
2012/0165686 A1    6/2012 Masuda et al.
2016/0022244 A1*  1/2016 Courtney .......... A61M 25/0045
600/466

* cited by examiner

MICRO-MECHANICAL ADJUSTMENT SYSTEM FOR PIEZOELECTRIC TRANSDUCERS

TECHNICAL FIELD

The disclosure is related generally to systems and methods for measuring blood velocity, and, in particular, to systems and methods for measuring blood velocity using phased arrays.

BACKGROUND

Currently, there is no non-invasive small wearable sensor which is able to detect the blood pressure of a human test subject. Non-invasive blood estimation has a lot of medical and personal benefits. In a lot of situations detecting the stress level of people could prevent heart attacks or avoid burn out diseases if the blood pressure is monitored over a longer period of time. Therefore there is the need of a sensor which is able to estimate blood pressure which enables to monitor the blood pressure over longer periods of time.

One of the main challenges of the measurement principle described in section will be to find the exact position of the artery in relation to the transducer array with a very high angle resolution. For the blood velocity measurement, it is necessary to know this angle precisely so the artery can be scanned correctly to achieve the best signal quality (SNR) and to minimize power in a wearable device. Therefore a new concept which is able to detect the position of the artery with high spatial and angular resolution will be proposed in this patent application.

DETAILED DESCRIPTION

Figure 1:
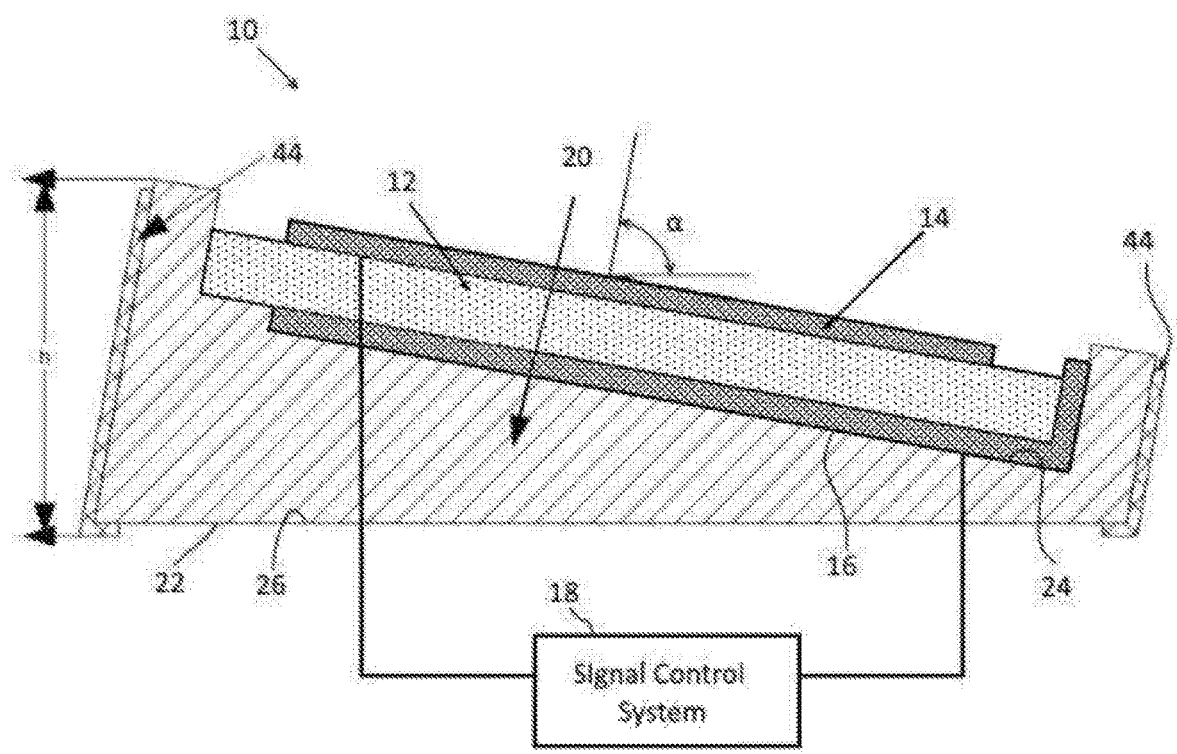
FIG. 1 depicts an ultrasonic piezoelectric transducer 10 according to one embodiment of the disclosure.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to one of ordinary skill in the art to which this disclosure pertains.

An ultrasonic piezoelectric transducer 10 according to one embodiment of the disclosure is depicted in FIG. 1. The ultrasonic piezoelectric transducer 10 includes a piezoelectric substrate 12, an upper electrode 14 and a lower electrode 16. The piezoelectric substrate 12 is formed of any suitable piezoelectric material including, for example, lead zirconate titanate or aluminium nitride. If the fabrication of the sensor device involves CMOS processes, aluminium nitride may advantageously be used because aluminium nitride is compatible with CMOS processes.

The upper and lower electrodes 14, 16 are formed of a conductive metal, such as aluminum, aluminum alloy, platinum, tantalum, or any other suitable conductive metal. As depicted schematically in FIG. 1, the upper and lower electrodes 14, 16 are configured to be electrically connected to a signal control system 18 which includes signal generating and/or receiving components.

The piezoelectric transducer 10 is supported on a carrier substrate 20. The carrier substrate 20 serves as a carrier for the piezoelectric transducer 10 and also as a coupling member for coupling the signals generated by the piezoelectric transducer 10 to underlying skin and tissue. The substrate 20 includes a lower surface 22 and an upper surface 24. The lower surface 22 of the substrate 20 is configured to be placed against a planar surface 26, such as a planar area of skin on a patient's body. The upper surface 24 is on an opposite side of the substrate from the lower surface 22 and is a generally planar surface to which the piezoelectric transducer 10 is attached.

The upper surface 24 is configured to orient the piezoelectric transducer 10 at a fixed non-zero angle with respect to the planar surface 26. To this end, the substrate 20 is fabricated in a manner that results in the upper surface 24 of the substrate 20 being tilted at a predetermined angle α with respect to the lower surface 22 of the substrate 20. The predetermined angle α corresponds to the desired angle of incidence at which the ultrasonic signals, or ultrasonic waves, emitted by the transducer.

The angle of incidence is the angle between a plane defined by the lower surface 22 of the substrate 20 or by the planar surface 26 and a line L that is perpendicular to the planar surface of the transducer 10 that intersects the plane.

The upper surface 24 of the substrate is configured to orient the piezoelectric transducer at a predetermined angle of incidence α that is greater than 0° and less than 90°. The predetermined angle of incidence α enables a single piezoelectric transducer 10 to be used to determine the blood velocity based on the Doppler Effect (explained in more detail below).

In addition to supporting the transducer 10 at a fixed incident angle α with respect to the planar surface 26, the substrate 20 is also configured to serve as a coupling member for coupling the ultrasonic signals between the piezoelectric transducer 10 and the underlying skin upon which the substrate is placed. Preferably, the substrate 20 is formed of steatite ceramic because steatite ceramic makes a dry transition to skin. Alternatively, any suitable substrate material may be used.

Figure 2:
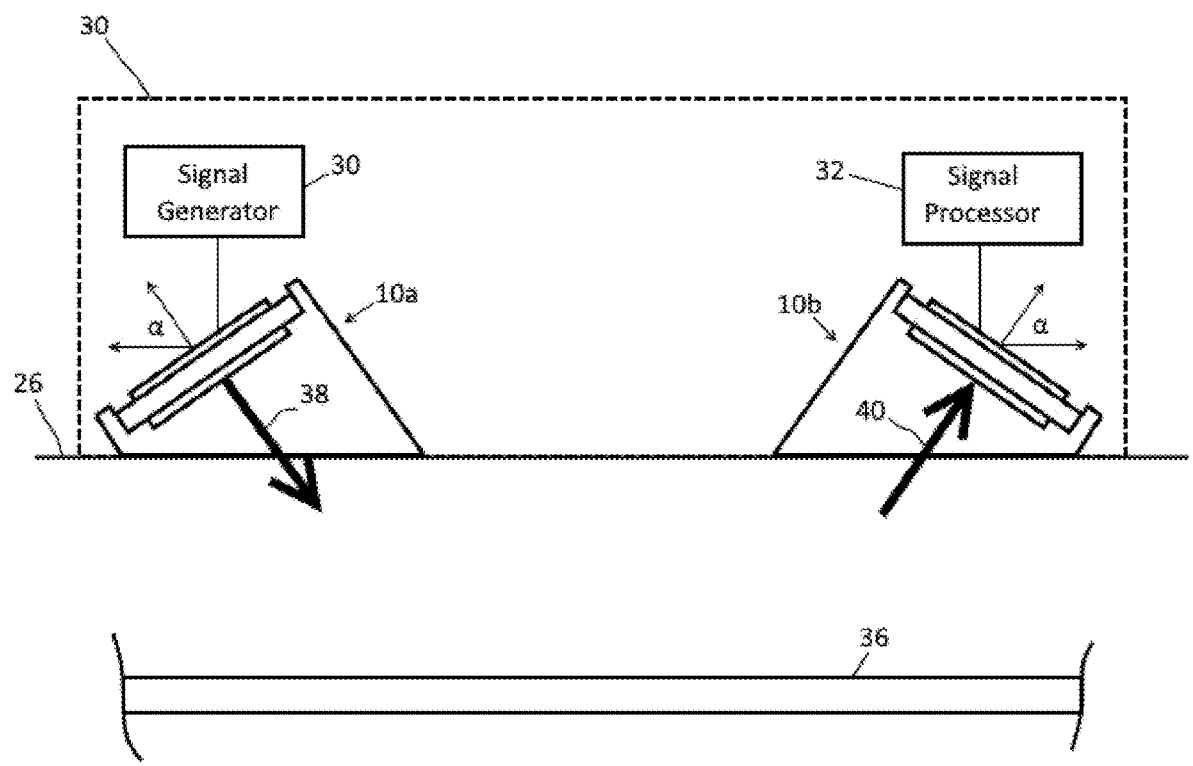
FIG. 2 depicts an embodiment of a system 30 for detecting blood velocity and measuring blood pressure using the piezoelectric transducer 10 of FIG. 1.

FIG. 2 depicts an embodiment of a system 30 for detecting blood velocity and measuring blood pressure using the piezoelectric transducer 10 of FIG. 1. The system 30 is a bistatic system including a single ultrasonic piezoelectric transmitter 10a and a single ultrasonic piezoelectric receiver 10b. The transmitter 10a and receiver 10b each have the same angle of incidence α and are arranged in mirror symmetry with respect to each other. In one embodiment, the transmitter and receiver 10a, 10b are incorporated into a housing 28 which retains the transmitter and receiver 10a, 10b at fixed positions in relation to each other. The housing 28 may be configured as a handheld device housing and/or may be incorporated into a wearable article which can be worn on a part of a user's body, such as the arm, leg or chest of a user.

The system 30 includes a signal generator 32 which is electrically connected to the piezoelectric transmitter 10a. The signal generator 32 is configured to actuate the piezoelectric transmitter 10a to produce a desired ultrasonic signal 38. To take advantage of the Doppler Effect to determine the blood velocity, the signal generator 32 is configured to actuate the piezoelectric transmitter 10a to transmit an ultrasonic signal in a pulsed or continuous wave fashion with a predetermined frequency. In one embodiment, the predetermined frequency is in a range from 2 MHz to 10 MHz. In one particular embodiment, the predetermined frequency is approximately 4 MHz.

The ultrasonic signal is directed toward the blood vessel 36 at an angle that depends on the angle of incidence α of the transducer 10a and is reflected by the blood vessel 36. The piezoelectric receiver 10b receives the reflected ultrasonic signal 40 and converts the signal to a corresponding electrical signal. A signal processor 34 is electrically connected to the piezoelectric receiver 10b and is configured to process the electrical signals to determine blood velocity in the blood vessel.

In one embodiment, the signal processor 34 is configured to evaluate the electrical signals from the piezoelectric receiver 10b to determine the radial velocity of the blood based on the Doppler Effect. For example, the received signal 40 has a Doppler shift due to the movement of the blood cells. The signal processor is configured to determine the Doppler shift of the received signal and to calculate a radial velocity of the blood as a function of the Doppler shift. The signal processor may be configured to determine the radial velocity of the blood from the Doppler shift in any suitable manner known in the art.

The signal processor may also be configured to determine a value for the blood pressure within the blood vessel. As is known in the art, there is a direct relationship between the blood velocity in a blood vessel and blood pressure. Therefore, once the blood velocity has been determined, an estimated value of the blood pressure can be determined as well. The signal processor may be configured to determine the blood pressure value from the blood velocity in any suitable manner.

For actuating the piezoelectric transducers 10a, 10b and processing received signals, the signal generating and processing devices 32, 34 may include a processor (not shown), such as a central processing unit, an application specific integrated circuit (ASIC), a field programmable gate array (FPGA) device, or a micro-controller. The processor may be configured to execute programmed instructions that are stored in a memory (not shown).

Figure 3:
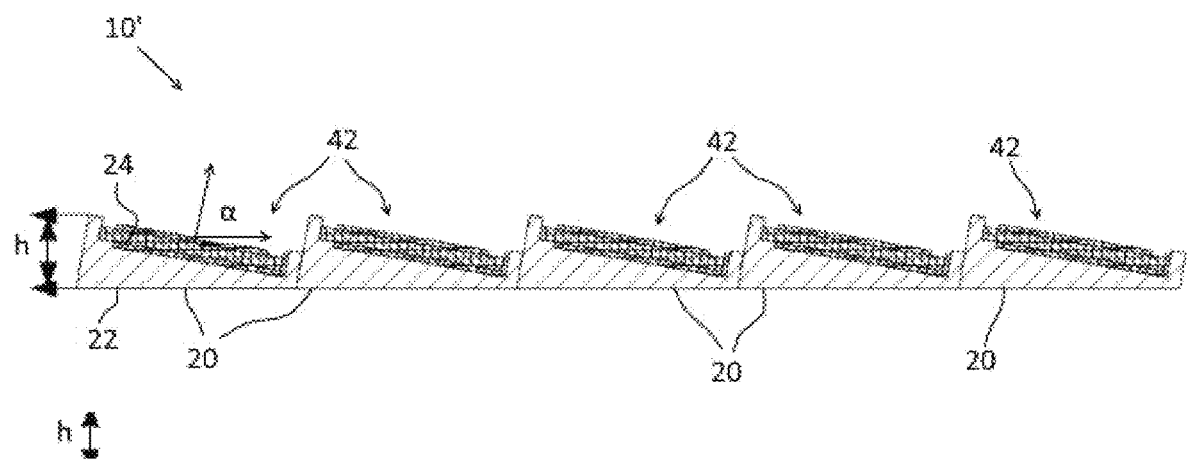
FIG. 3 depicts an alternative embodiment of a piezoelectric transducer for use with the system of FIG. 2.

Referring now to FIG. 3, an alternative embodiment of a piezoelectric transducer 10' is depicted which may be used with the blood velocity detection and blood pressure measurement system 30 of FIG. 2. The piezoelectric transducer 10' of FIG. 3 is a distributed piezoelectric transducer. The distributed piezoelectric transducer 10' is formed by dividing the piezoelectric transducer 10 of FIG. 1 along one dimension into a plurality of separate, smaller transducers 42. The plurality of transducers 42 are connected together in a row and operated as a single piezoelectric transducer.

As depicted in FIG. 3, each of the transducer elements 42 is provided on a separate substrate which is preferably formed of steatite ceramic. The upper surface 24 of each of the substrates 20 is a planar surface that is arranged to provide an angle of incidence α that is greater than 0° and less than 90° in the same manner as the upper surface 22 of the substrate 20 in FIG. 1. Because the transducer elements 42 are smaller than the transducer 10 of FIG. 1, the distributed transducer 10' can have the same effective width as the single element transducer 10 of FIG. 1 while enabling a significant reduction in height h as compared to the transducer 10 of FIG. 1. Higher angles of incidence therefore can be achieved with a distributed transducer without resulting in a significant increase in the overall height of the transducer.

Figure 4:
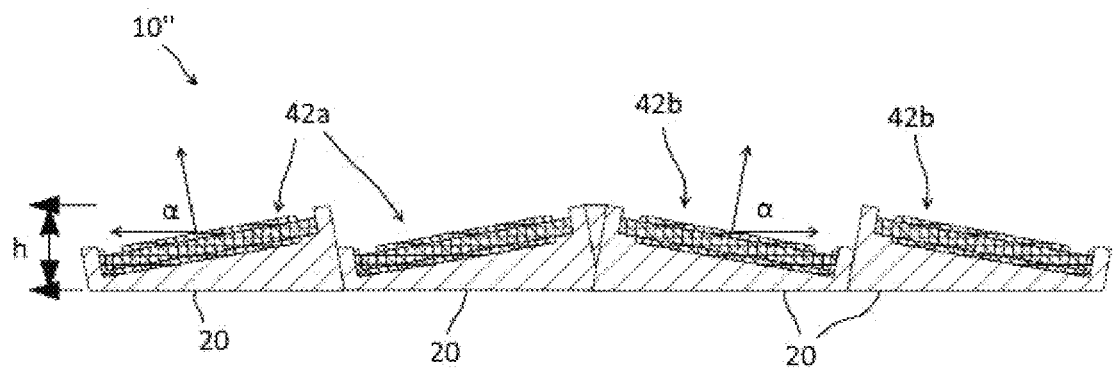
FIG. 4 depicts another alternative embodiment of a piezoelectric transducer for use with the system of FIG. 2.

In the embodiment of FIG. 3, the plurality of transducers 42 form one row of transducers, i.e. a 1×N array where N is the number of transducer elements (five in this case). Each of the transducers 42 is oriented in the same direction with the same angle of incidence α. In alternative embodiments, the transducers 42 can be provided with different angles of incidence and can be oriented in different directions. FIG. 4 depicts an embodiment of a distributed transducer 10'' having transducer elements 42a, 42b which are oriented in two different directions. In this embodiment, each of the transducer elements 42a, 42b is configured to have the same angle of incidence. The transducer 10'' of FIG. 4 could be configured as a bistatic system with the elements 42a being grouped together to serve as a transmitter and elements 42b being grouped together to form a receiver. In another example (not shown), the transducer elements could be arranged to form pyramid structures in which four transducer elements are oriented in four different directions with the same angle of incidence.

To avoid coupling between the different transducer elements 42, an isolation layer 44 may be added onto the edges of the substrate 20 to damp or reflect ultrasound signals from adjacent transducer elements 42. An example of an isolation layer 44 on a transducer is depicted in FIG. 1. Any suitable type of material may be used for the isolation layer 44.

Referring now to FIGS. 5-10, another embodiment of a system 30 for detecting blood velocity and measuring blood pressure is depicted. In the embodiment of FIGS. 5-10, the system 45 includes a phased transducer array 46 for generating and receiving the ultrasonic signals which are used to detect artery location and measure blood velocity.

Figure 5:
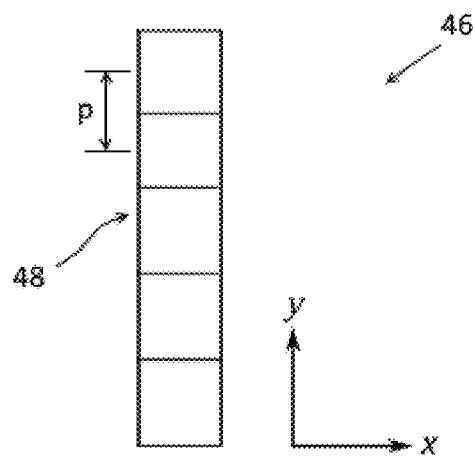
FIG. 5 depicts a 1×N array of transducer elements for a phased transducer array.
Figure 6:
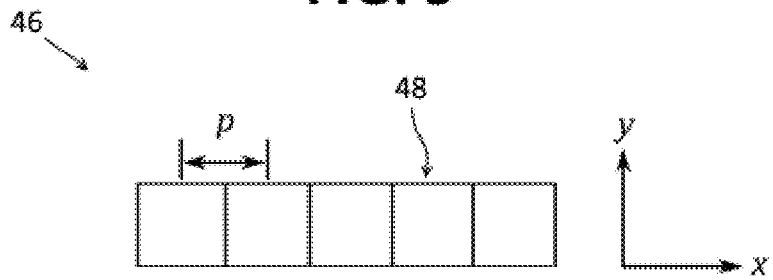
FIG. 6 depicts an N×1 array of transducer elements for a phased transducer array.
Figure 7:
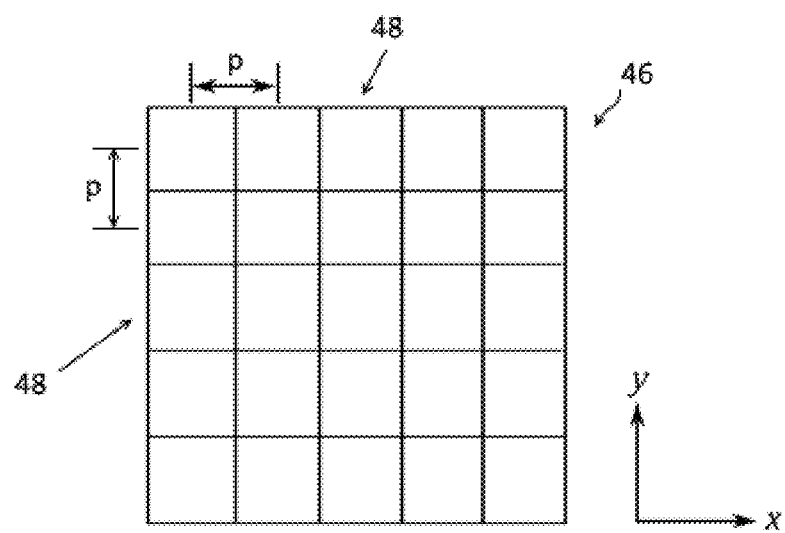
FIG. 7 depicts an M×N array of transducer elements for a phased transducer array.

A phased transducer array 46 includes an array of piezoelectric transducer elements 48 arranged on a substrate. The transducer array 46 may comprise any number of elements along the X axis and Y axis of the array. For example, the array may comprise a 1×N array of transducers as depicted in FIG. 5 which has one element along the X axis and N (in this case five) elements along the Y axis, or the array may comprise an N×1 array as depicted in FIG. 6 where N elements (in this case five) are provided along the X axis and one element is provided along the Y axis. A transducer array having a dimension with a single element is also referred to as a transducer row. The array 46 may also comprise an M×N array of transducers where M is the number of elements in along the X axis of the array and N is the number of elements along the Y axis of the array and M and N are greater than one. In FIG. 7, the array is a 5×5 array of transducer elements 48.

The parameter p is the pitch distance between the center of one transducer element 48 and the center of an adjacent transducer element 48. The distance p is advantageously smaller than half the wavelength of the signal emitted by the array. The wavelength of signal is given by the following equation:

$$\lambda = v/f$$

where $\lambda$ is the wavelength of the signal, v is the ultrasonic velocity (for PZT: v≈3200 m/s, for human tissue: v≈1560 m/s), and f is the frequency of the signal. For a transducer array to be operated around a frequency of 4 MHz, the wavelength is approximately 0.80 mm. Therefore, the pitch p in this case should be approximately 400 μm.

In one embodiment, each transducer element 48 has substantially the same size and shape with the shape of each element being rectangular or square. The transducer elements 48 in the array 46 are fed an electrical signal from a phase control system 62 simultaneously which causes each transducer element 48 to emit an ultrasonic signal or wave.

As is known in the art, the phase of the signals being fed to the different elements may be controlled so that the effective radiation pattern of the array is reinforced in a desired direction and suppressed in undesired directions so that the main lobe, or beam, of the radiation pattern is pointed in the desired direction. By adjusting the phases of the signals fed to the elements, the direction of the beam may be changed in a process called beam steering. Accordingly, an adjustable phase shifter (not shown) is associated with each element 48 in the array 46 which enables the phase of the electrical signal being fed to the transducer element 48 to be shifted.

Figure 8:
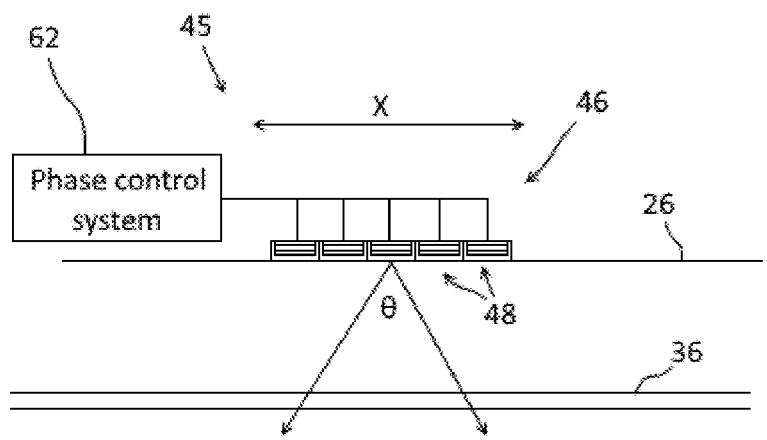
FIG. 8 is a schematic depiction of a phased transducer array with beam steering along an X axis of the array.
Figure 9:
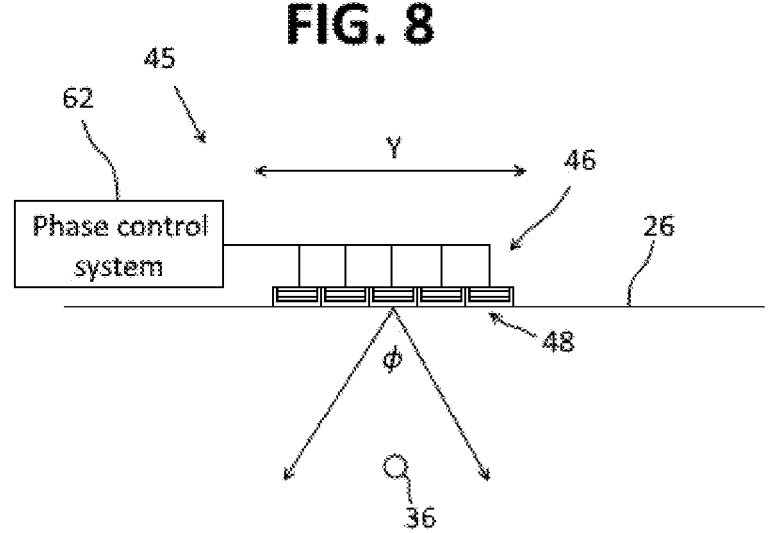
FIG. 9 is a schematic depiction of a phased transducer array with beam steering along an Y axis of the array.
Figure 10:
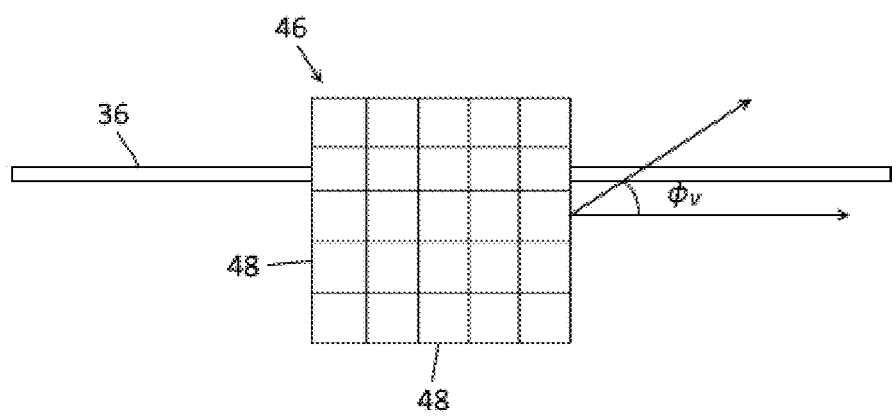
FIG. 10 is a schematic depiction of a phased transducer array depicting a measurement angle for the transducer.

As depicted in FIG. 8, a phased array 46 having more than one element 48 along the X axis (i.e., the axis parallel to the longitudinal dimension of the blood vessel and the direction of blood flow) enables beam steering along the X axis. This enables the angle component $\theta$ of the beam to be adjusted. The angle component $\theta$ controls the angle of incidence of the beam with respect to the blood vessel 36. Similarly, a phased array 46 having more than one element 48 along the Y axis (i.e., the axis perpendicular to the blood vessel and the direction of blood flow) enables beam steering along the Y axis as depicted in FIG. 9. This enables the angle component $\phi$ to be adjusted. With the angle component $\theta$ set to the angle of incidence for the transducer 46, scanning the beam along the Y axis can be used to find the measurement angle $\phi_v$ where the blood vessel 36 is located as depicted in FIG. 10.

A phased array control system 62 is used to control the phase shifting of the transducer elements 48 to produce a beam in the desired direction. The control system 62 includes a processor (not shown), such as a central processing unit, an application specific integrated circuit (ASIC), a field programmable gate array (FPGA) device, or a microcontroller. The processor may be configured to execute programmed instructions that are stored in the memory (not shown). The instructions include instructions for phase shifting and/or for implementing one or more beam steering algorithms.

Figure 11:
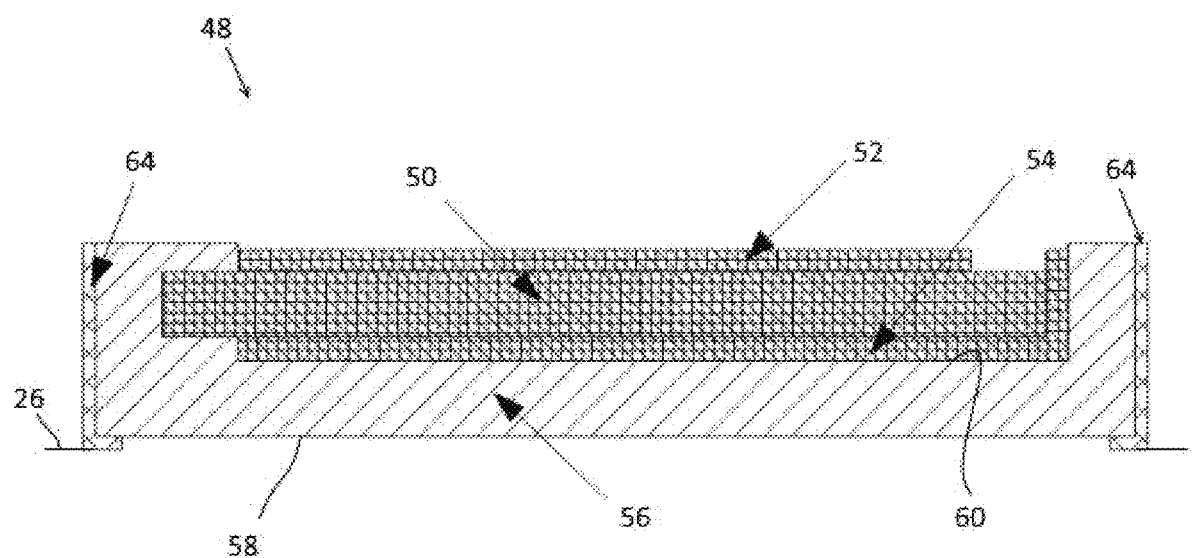
FIG. 11 depicts an embodiment of a transducer element for a phased transducer array.

An embodiment of a transducer element 48 for use in a phased transducer array is depicted in FIG. 11. Similar to the transducer of FIG. 1, the transducer element 48 includes a piezoelectric substrate 50, an upper electrode 52 and a lower electrode 54. The piezoelectric substrate 50 is formed of any suitable piezoelectric material including, for example, lead zirconate titanate or aluminium nitride. The upper and lower electrodes 52, 54 are formed of a conductive metal, such as aluminum, aluminum alloy, platinum, tantalum, or any other suitable conductive metal.

The transducer element 48 is supported on a carrier substrate 56. The carrier substrate 56 serves as a carrier for the transducer element 48 and also as a coupling member for coupling the ultrasonic signals to underlying skin and tissue. The substrate 56 includes an lower surface 58 and an upper surface 60. The lower surface 58 is configured to be placed against a planar surface 26, such as a planar area of skin on a patient's body. The upper surface 60 is on an opposite side of the substrate from the lower surface 58 and is a generally planar surface to which the transducer element 48 is attached.

To avoid coupling between the different transducer elements 48 of the array 46, an isolation layer 64 may be added onto the edges of the substrate 56 to damp or reflect ultrasound signals from adjacent transducer elements 48. Any suitable type of material may be used for the isolation layer 64.

The upper surface 60 is configured to orient the transducer element 48 with respect to the surface 26 of the skin. For a two-dimensional array, such as depicted in FIG. 7, beam steering can be used to adjust the angle component $\theta$ so a fixed angle of incidence is not required for the transducer. Therefore, the transducer can be arranged parallel to the surface 26 which results in the transducer lying substantially flat on the substrate.

In one embodiment of the system 45, the angle of incidence of the transducer elements 48 is set to a fixed value which enables the radial component of the blood velocity to be determined. This can be accomplished by actuating the transducer elements 48 with static, phase shifted electrical signals that cause the beam to be emitted at the desired angle of incidence. The transducer elements arrayed along the Y axis enable beam steering to be used to locate the measurement angle $\phi_v$ in which the blood vessel 36 is located (FIG. 10). In this embodiment, the system may be configured as a bistatic system, such as depicted in FIG. 2, with one phased transducer array configured as a transmitter and one phased transducer array configured as a receiver.

In an alternative embodiment, the phased array 46 of may be provided as a transducer row with a single element width along the X axis to reduce the number of elements required for the array. In this embodiment, angle of incidence of each element 48 is fixed to enable the radial component of the blood velocity to be determined. This can be accomplished in the same manner as in the embodiment of FIG. 1, e.g., by orienting the upper surface of the substrate at the desired angle of incidence.

Figure 12:
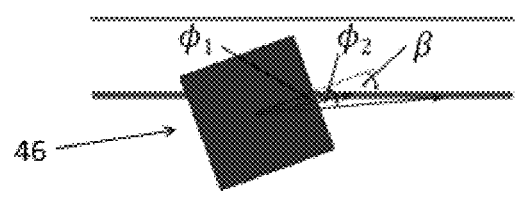
FIG. 12 schematically depicts a phased array transducer misaligned with respect to a blood vessel.

The use of phased array transducers enables correction of misalignment of the transducer array 46 with respect to the blood vessel 36. For example, FIG. 12 depicts a phased transducer array 46 which is misaligned with respect to the blood vessel 36 by an angle β. To compensate for the misalignment during the determination of the radial velocity of the blood, the angle β must be determined. This can be done using a triangulation method. More specifically, the angle β may be determined using the angle θ which corresponds to the incident angle and the angle φ which is related to the measurement angle where the blood vessel 36 is located.

Figure 13:
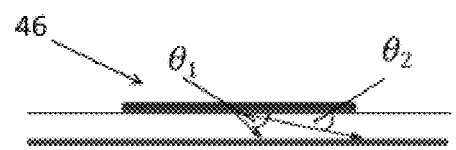
FIG. 13 schematically depicts a side view of the phased array transducer of FIG. 12.

Referring to FIGS. 12 and 13, to determine the misalignment angle β, the phased transducer array 46 is actuated at a first angle $\theta_1$, and the measurement angle $\phi_1$ at which the blood vessel 36 is located is identified. The beam is then steered to a second angle $\theta_2$, and the measurement angle $\phi_2$ at which the blood vessel 36 is located is identified. The distances to the blood vessel 36 at the first and the second measurement angles $\phi_1$, $\phi_2$ can then be determined which enables the blood flow direction to be identified. Because the central axis of the array 46 is known, the misalignment angle β can be determined so that the misalignment angle β can be compensated for in calculating the radial component of the blood velocity.

Figure 14:
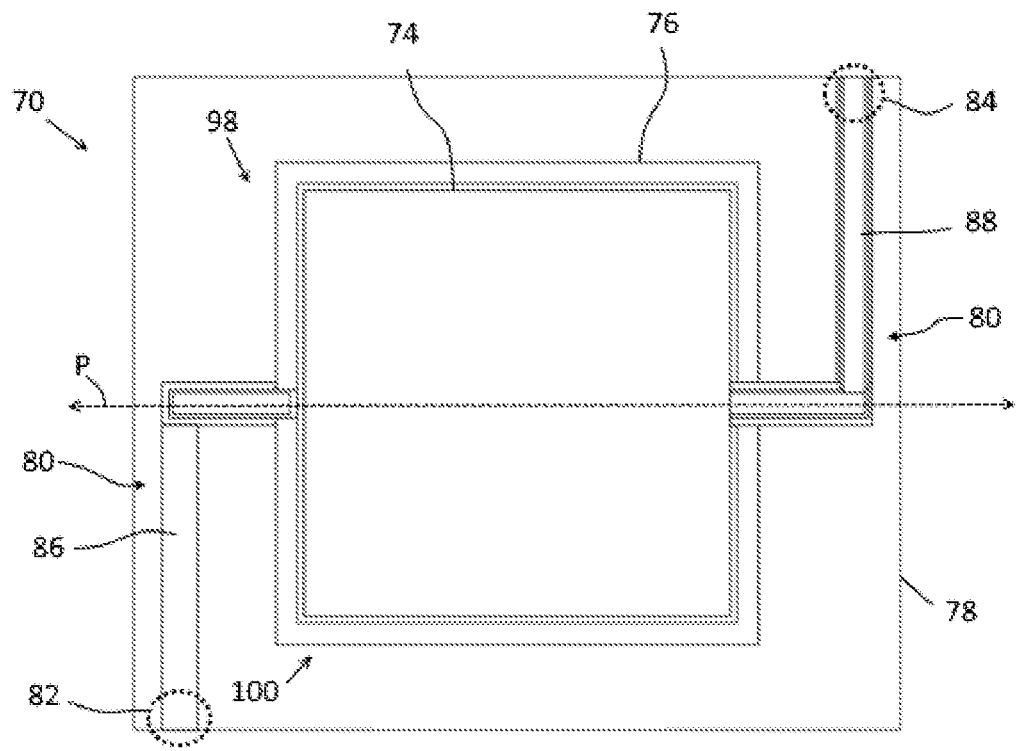
FIG. 14 is a top view of a piezoelectric transducer having micro-mechanical adjustment means.
Figure 15:
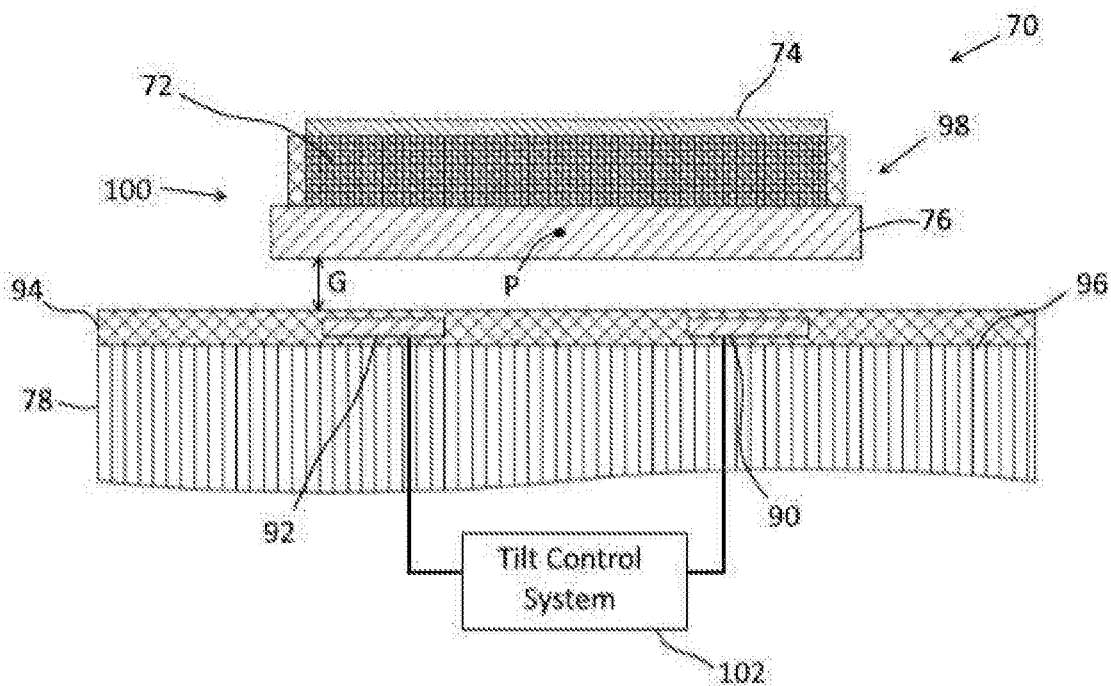
FIG. 15 is an elevational view of a first side of the transducer of FIG. 14.
Figure 16:
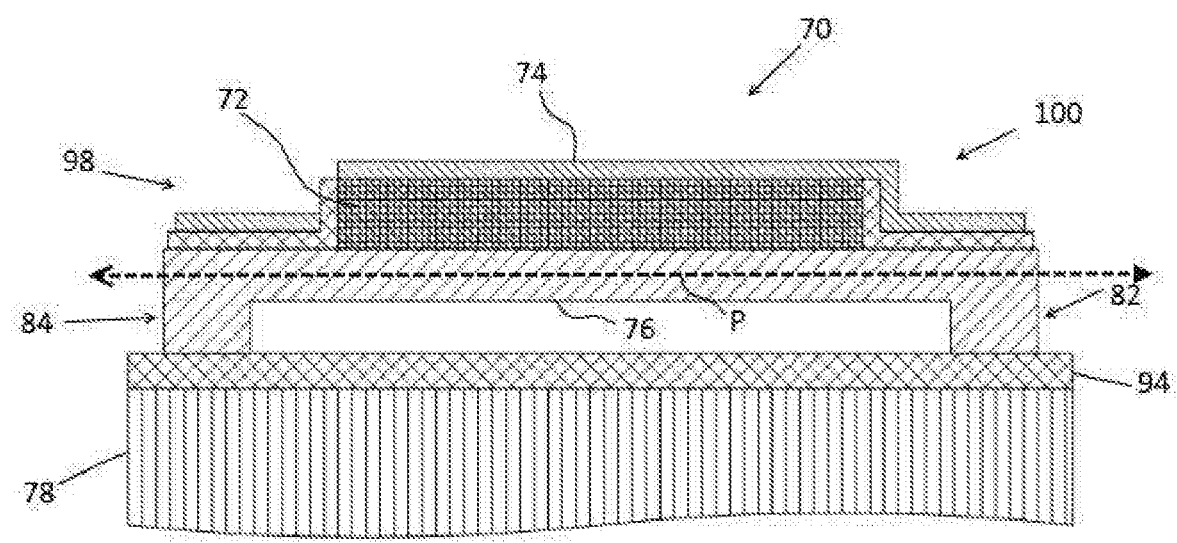
FIG. 16 is an elevational view of a second side of the transducer of FIG. 14.

As an alternative to beam steering with phase shifting, micro-mechanical mechanisms may be used to adjust the incident angle and/or the measurement angle of the transducer in compensating for misalignment of the transducer with respect to the blood vessel. An embodiment of a piezoelectric transducer having a micro-mechanical adjustment mechanism is depicted in FIGS. 14-16. As depicted, the piezoelectric transducer 70 includes a piezoelectric substrate 72, an upper electrode 74 and a lower electrode 76. The upper and lower electrodes 74, 76 are formed of a conductive material, such as poly-silicon. The piezoelectric substrate 72 is formed of a suitable piezoelectric material, such as lead zirconate titanate or aluminium nitride.

Figure 17:
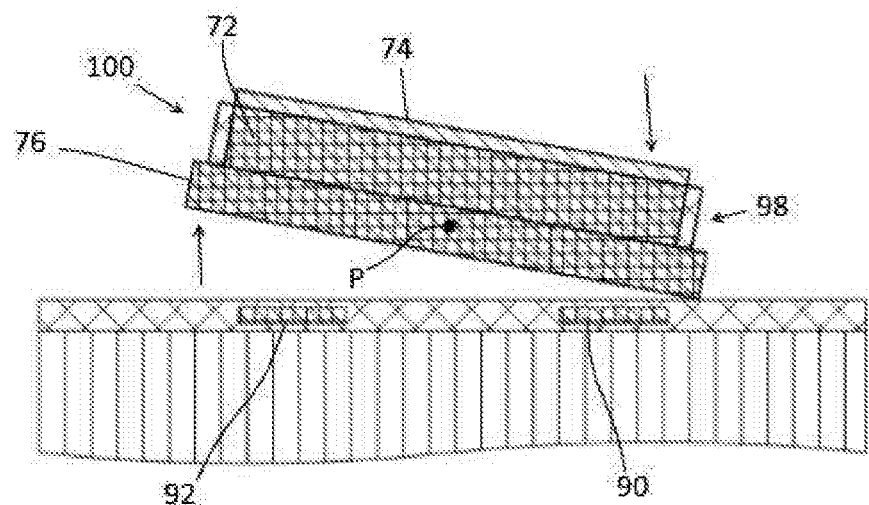
FIG. 17 shows the piezoelectric transducer of FIG. 14 in a first tilted position.
Figure 18:
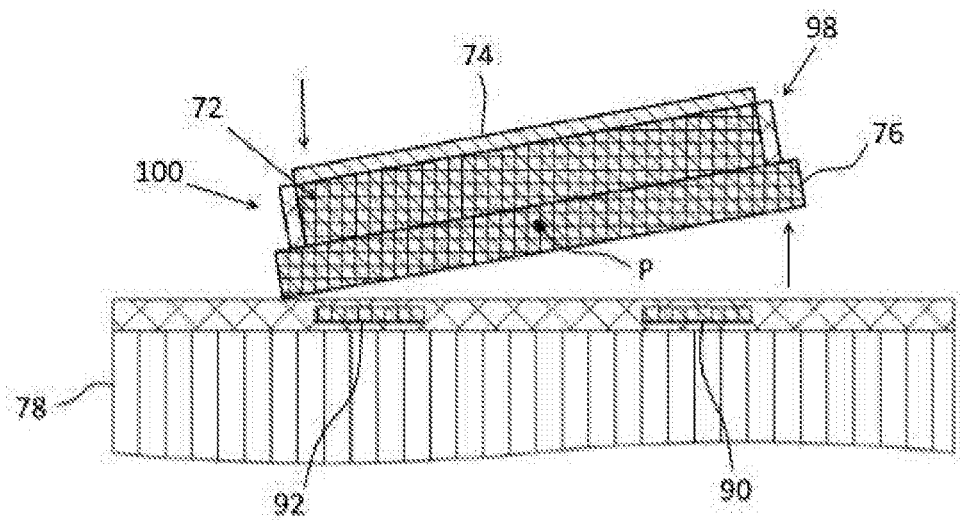
FIG. 18 shows the piezoelectric transducer of FIG. 14 in a second tilted position.

The transducer 70 comprises an element of a phased array 46, such as depicted in FIGS. 5-10. The transducer 70 is supported on a carrier substrate 78 which may be formed of silicon although any suitable material may be used. The transducer 70 is suspended over the substrate 78 by a micro-mechanical adjustment system 80 that enables the transducer 70 to pivot about a pivot axis P between a first tilted position (FIG. 17) and a second tilted position (FIG. 18). The micro-mechanical adjustment system 80 includes one or more spacers 82, 84 which are configured to space the transducer 70 apart from the substrate 72 to form a gap G between the substrate 78 and the lower electrode 76.

In the embodiment of FIGS. 14-16, the adjustment system 80 includes a first spacer 82 and a second spacer 84. As depicted in FIG. 14, the first spacer 82 is positioned proximate a first corner of the substrate 78 outside of the region over which the transducer 70 is located, and the second spacer 84 is positioned proximate a second corner which is opposite from the first corner and outside the region of the substrate over which the transducer 70 is located.

The first and second spacers 82, 84 are connected to the transducer 70 by first and second support arms 86, 88, respectively. The first support arm 86 extends from an upper portion of the first spacer 82 and is connected to the upper electrode 74 of the transducer 70, and the second support arm 88 extends from the upper portion of the second spacer 84 and is connected to the lower electrode 76 of the transducer 70. The first and second spacers 82, 84 and the first and second support arms 86, 88 are formed of an electrically conductive material, such as poly-silicon, and are used to electrically connect the upper and lower electrodes 74, 76, respectively, to control and read-out circuitry.

The tilting of the transducer 70 to the first and second tilted positions is controlled by setting electrodes 90, 92 which are provided on or in the upper portion of the substrate 78. The setting electrodes 90, 92 are formed of a conductive material, such as poly-silicon. In the embodiment of FIG. 15, the setting electrodes 90, 92 are formed in an insulator layer 94 formed on the upper surface 96 of the substrate 78. The insulator layer 94 is formed of an insulating material, such as silicon dioxide.

The setting electrodes comprise a first setting electrode 90 and a second setting electrode 92. The first setting electrode 90 is located on the substrate 78 under a first side portion 98 of the transducer 70 which is positioned on a first side of the pivot axis P. The second setting electrode 92 is located on the substrate 78 under a second side portion 100 of the transducer 70 which is positioned on a second side of the pivot axis P. The first and second setting electrodes 90, 92 are isolated from each other by the insulator layer 94.

As depicted schematically in FIG. 15, a tilt control system 102 is electrically connected to the first and second setting electrodes 90, 92. The tilt control system 102 is configured to selectively apply a bias voltage to the setting electrodes 90, 92 for causing the transducer 70 to pivot to the first and the second tilted positions.

When the tilt control system 102 applies the bias voltage to the first setting electrode 92, a potential difference is created between the first setting electrode 90 and the lower electrode 76 on the first side portion 98 of the transducer which causes the first side portion 98 of the transducer 70 to be drawn downwardly toward the substrate 78. As the first side portion 98 moves downwardly, the transducer 70 pivots toward the first tilted position (FIG. 17) resulting in the second side portion 100 of the transducer 70 moving upwardly, farther away from the substrate 78.

When the tilt control system 102 applies the bias voltage to the second setting electrode 92, a potential difference is created between the second setting electrode 92 and the lower electrode 76 on the second side portion 100 of the transducer 70 which causes the second side portion 100 to be drawn downwardly toward the substrate 78. As the second side portion 100 moves downwardly, the transducer 70 pivots toward the second tilted position (FIG. 18) resulting in the first side portion 98 of the transducer moving upwardly, farther away from the substrate 78.

When the bias voltage is applied to the first setting electrode 90, the transducer 70 pivots until the first side portion 98 contacts the substrate 78 or the insulator layer 94 on the substrate 78. The orientation of the transducer 70 when the first side portion 98 contacts the substrate 78 corresponds to the first tilted position (FIG. 17). When the bias voltage is applied to the second setting electrode 90, the transducer 70 pivots until the second side portion 100 contacts the substrate 78 or the insulator layer 94 on the substrate 78. The orientation of the transducer 70 when the second side portion 100 contacts the substrate 78 corresponds to the second tilted position (FIG. 18). In alternative embodiments, other structures may be incorporated onto the substrate and/or the bottom of the lower electrode to serve as stops for limiting the movement of the transducer toward the substrate and setting the first and second tilted positions.

In an unbiased state, the transducer 70 is oriented substantially parallel to the upper surface 96 of the substrate 78, as can be seen in FIGS. 15 and 16, which results in the transducer 70 having substantially a 0° angle of incidence with respect to the blood vessel. When the transducer is in the first tilted position, the transducer 70 is oriented in a first direction at an angle of incidence α that is greater than 0° and less than 90°. When the transducer 70 is in the second tilted position, the transducer 70 is oriented in the opposite direction at the same angle of incidence α. In alternative embodiments, the angle of incidence of the transducer may be different in the first and second tilted positions. This may be accomplished by incorporating asymmetric stops or limit structures onto the device for limiting movement of the transducer to different degrees in the different directions of tilt.

The micro-mechanical adjustment system 80 can be used to compensate for misalignment of the transducer 70 with respect to the blood vessel 30 in a similar manner as described above with regard to the phased array transducer of FIGS. 5-10. In this embodiment, movement of the transducer 70 to the angles $\theta_1$ and $\theta_2$ is accomplished mechanically via the micro-mechanical adjustment system 80 by application of the bias voltage to the appropriate setting electrode 90, 92. Beam steering with phase shifting is then used to find the measurement angles $\phi_1$, $\phi_2$ where the blood vessel is located for the angles $\theta_1$ and $\theta_2$. The distances to the blood vessel at the first and the second measurement angles $\phi_1$, $\phi_2$ can then be determined which enables the blood flow direction to be identified. Because the central axis of the array is known, the misalignment angle β can be determined so that the misalignment can be compensated for in calculating the radial component of the blood velocity.

In the embodiment of FIGS. 14-18, because the angle of incidence is adjusted mechanically, beam steering is not required to redirect the beam so the array of transducers needs fewer transducers along the X axis. Therefore, in one embodiment, the array of transducers has a width along the X axis corresponding to one transducer element. The number of transducers along the Y axis may be any suitable number that provides the desired angle resolution and aperture size for finding the measurement angle where the blood vessel is located.

The micro-mechanical adjustment system 80 of the embodiment of FIGS. 14-18 is configured to enable mechanical adjustments of only one angle of the transducer. In alternative embodiments, mechanical adjustment systems may be configured to enable mechanical adjustments of only the measurement angle of the transducer while enabling adjustments of the incident angle by beam steering with phase shifting.

In another alternative embodiment, the micro-mechanical adjustment system may be configured to enable mechanical adjustments of both the angle of incidence and the measurement angle of the transducer. The transducer array comprises an array of piezoelectric transducer elements, such as depicted in FIGS. 5-7. The array may comprise a 1×N array, an N×1 array, or an M×N array.

In this embodiment, the adjustment system and the transducer may be configured similar to a two-axis micro-mirror to enable tilting of the transducer about two perpendicular axes. This embodiment eliminates the need for phase shifters all together as beam steering is not required to adjust the angles of the transducer.

Figure 19:
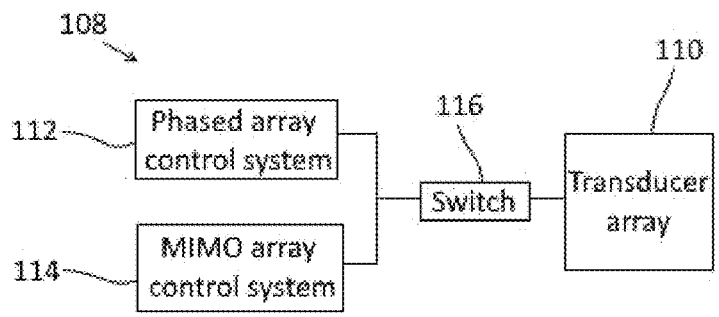
FIG. 19 is a block diagram of a combined multi-input multi-output (MIMO) array and phased array blood velocity detection system.

Another embodiment of a system 108 for detecting blood velocity and measuring blood pressure is depicted in FIG. 19. In this embodiment, the piezoelectric transducer arrangement of the system is configured to implement both a multi-input multi-output (MIMO) ultrasonic transducer array and a phased transducer array. The system includes at least one ultrasonic transducer array 110, a phased array control system 112 and a MIMO array control system 114.

The transducer array 110 may comprise any number of elements along the X axis and Y axis of the array. For example, the array may comprise a 1×N array, an N×1 array, or an M×N array, as depicted in FIGS. 5-7, respectively. The elements in the array may also be shifted, staggered or offset from each other in either direction.

Figure 20:
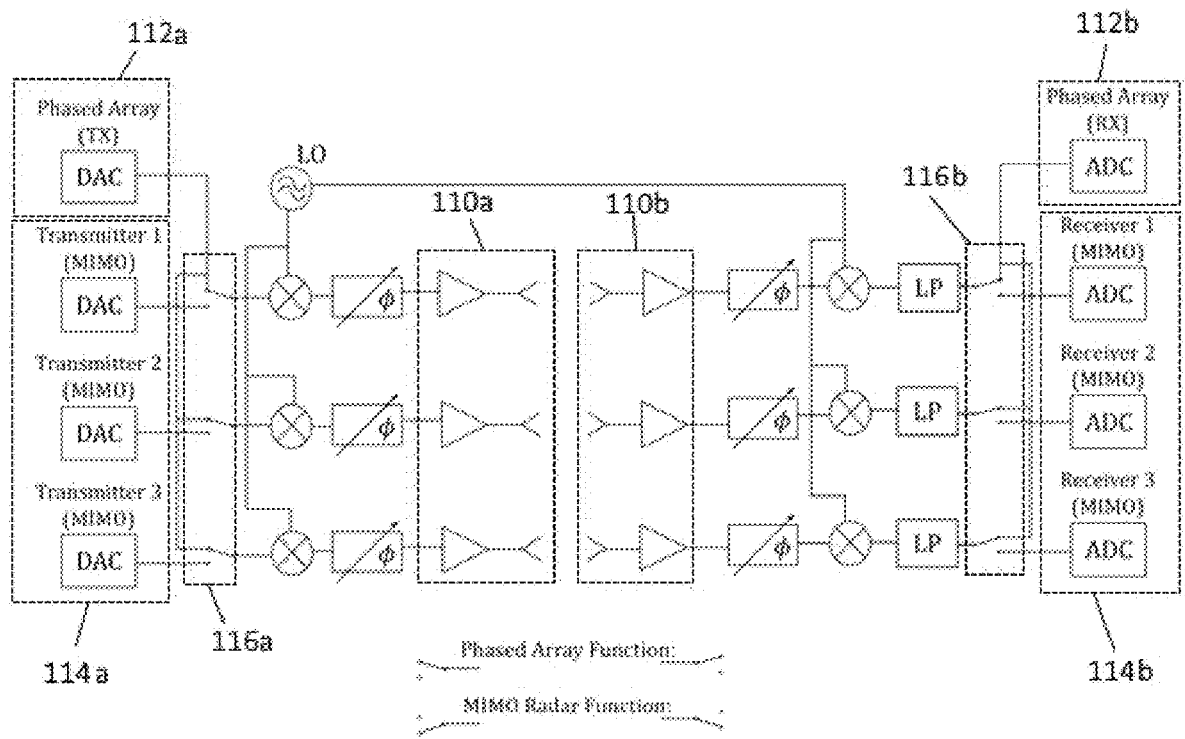
FIG. 20 is a schematic diagram of a bistatic version of the combined multi-input multi-output (MIMO) array and phased array blood velocity detection system of FIG. 19.

The system 108 may comprise a monostatic system in which the transducer array 110 is used for both transmitting and receiving ultrasonic signals. Alternatively, the system may comprise a bistatic system as depicted in FIG. 20. In a bistatic system, a first ultrasonic transducer array 110a serves as the transmitter for the system and a second ultrasonic transducer array 110b serves as the receiver for the system.

Transducers used to transmit are operably coupled to receive electrical signals from the phased array control system 112a and the MIMO array control system 114a. Transducers used to receive output electrical signals to the phased array control system 112b and the MIMO array control system 114b. The phased array control system 112b and the MIMO array control system 114b are configured to process the electrical signals using various techniques and algorithms known in the art to determine information about the blood vessel.

The piezoelectric transducer elements of the array can have the same configuration as any of the transducer elements of the embodiments discussed above. Using the transducer element of FIG. 11 as an example, each transducer element of the array includes a piezoelectric substrate 50, an upper electrode 52 and a lower electrode 54. The upper and lower electrodes 52, 54 are formed of a conductive material, such as poly-silicon. The piezoelectric substrate 50 is formed of a suitable piezoelectric material, such as lead zirconate titanate or aluminium nitride. In one embodiment, each transducer element has substantially the same size and shape with the shape of each element being rectangular or square.

To avoid grating lobes when the transducer array is operated as a phased array, the pitch distance between the centers of adjacent elements in the array is advantageously smaller than half the wavelength of the signal emitted by the array. As noted above, for a transducer array to be operated around a frequency of 4 MHz, the wavelength is approximately 0.80 mm. Therefore, the pitch should be approximately 400 μm.

The phased array control system 112a is configured to supply the transmitting transducers with the same electrical signal, or waveform, with phase shifting and amplitude setting to direct an ultrasonic beam in the desired direction. The use of multiple transducers to transmit and receive the same signal results in significant transducer gain and good signal quality.

The MIMO array control system 114a is configured to supply each of the transmitting transducers with an arbitrary waveform. To this end, the MIMO array control system 114a includes a waveform generator (not shown) for each of the transducers. The waveform generators are configured to generate different waveforms for each of the transducers. These waveforms can be either correlated or uncorrelated with each other and can be separated in the temporal, spectral, and/or spatial domains. It is also important that the waveforms do not interfere with each other. One way to accomplish this is with a time-division multiplexing (TDM)-switched MIMO.

Each receiving transducer receives reflected signals from each of the transmitting transducers. Due to the different wave forms, the reflected signals can be associated with the transmitting transducer which emitted them. A transmitting array of N transducers and a receiving array of K transducers results in a K×N virtual array from K+N elements. This enables MIMO arrays to have large virtual apertures and a higher angle of resolution than corresponding phased arrays.

The phased array and MIMO array control systems may each include a processor (not shown), such as a central processing unit, an application specific integrated circuit (ASIC), a field programmable gate array (FPGA) device, or a micro-controller. The processor may be configured to execute programmed instructions that are stored in the memory (not shown). The instructions include instructions for phase shifting and/or for implementing one or more beam steering algorithms.

The blood velocity detection system 108 includes a switching devices 116a, 116b that are configured to switch the inputs to the transmitting arrays 110a and the outputs of the receiving arrays 110b between the phased array control system 112a, 112b and the MIMO array control system 114a, 114b, respectively, so that the transducer arrays can be operated as both a phased transducer array and a MIMO transducer array as needed. Any suitable switching configuration and/or methodology may be used for the switching devices 116a, 116b.

In operation, the inputs to the transducer arrays are first switched to the MIMO array control system 114 so that the transducer array 110 is operated as a MIMO transducer array. The MIMO array control system 114 supplies the transmitting transducers 110a with arbitrary distinct waveforms which causes the transducers to emit ultrasonic signals which are directed roughly in the direction of the blood vessel. Reflected signals are received by the receiving transducers 110b. The MIMO array control system 114 evaluates the output of the receiving transducers to locate the blood vessel.

The input to the transducer arrays 110a, 110b are then switched to the phased array control system 112a, 112b so that the transducer array is operated as a phased transducer array to take advantage of the high transducer gains and better signal quality of the phased transducer array and because the incident and outgoing beam can be directed by beam steering with phase shifting.

One object of the combined MIMO array and phased array blood velocity detection system is avoiding the use of high resolution algorithms, such as multiple signal classification (MUSIC) algorithms. To accomplish this, the transducers may be actuated as a sparse transducer array. The transducer array may be operated as a sparse array by omitting some of the transducer elements from being actuated to produce ultrasonic signals. In one embodiment, the transducers may be omitted from actuation as part of the MIMO transducer array in a random pattern so that different pitches, or spacings, are provided between elements in the array. The sparse spacing allows even larger virtual aperture sizes which in turn results in higher angle resolutions. This gives the opportunity to achieve a better spatial/angle resolution and make a better angle estimation so that the blood vessel is located with greater accuracy.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A system for detecting blood velocity within a blood vessel, the system comprising:
   a transducer array configured to be placed on an area of skin of a person over the blood vessel, the transducer array including a plurality of ultrasonic piezoelectric transducers, each of the piezoelectric transducers including:
     a carrier substrate having an upper surface; a first spacer and a second spacer extending upwardly from the upper surface;
     a transducer element supported above the upper surface of the carrier substrate by the first spacer and the second spacer, and the transducer element is spaced apart from the upper surface of the substrate;
     an upper electrode positioned on an upper surface of the transducer element facing away from the carrier substrate;
     a lower electrode positioned on a lower surface of the transducer element facing toward the carrier substrate; and
     setting electrodes positioned on the upper surface of the substrate under the transducer element, and the setting electrodes configured to receive a bias voltage,
     wherein the bias voltage being configured to create a potential difference between the setting electrodes and the lower electrode and the transducer element is configured to pivot about a pivot axis between a first tilted position and a second tilted position by the potential difference,
     wherein the first spacer and the second spacer are each positioned on the upper surface outside of a region over which the transducer element is located, the first spacer being connected to a first lateral portion of the transducer element by a first support arm that extends from an upper portion of the first spacer, the second spacer being connected to a second lateral portion of the transducer element by a second support arm that extends from an upper portion of the second spacer, and
     wherein the transducer element defines a first angle with respect to the blood vessel in the first tilted position and a second angle with respect to the blood vessel in the second tilted position.

2. The system of claim 1, wherein the setting electrodes include a first setting electrode and a second setting electrode, the first setting electrode being positioned under a first side portion of the transducer element, the first side portion being located on a first side of the pivot axis, the second setting electrode being positioned under a second side portion of the transducer element, the second side portion being located on a second side of the pivot axis.

3. The system of claim 2, wherein, in the first tilted position, the transducer element defines a first angle of incidence with respect to the blood vessel, and, in the second tilted position, the transducer element defines a second angle of incidence with respect to the blood vessel.

4. The system of claim 3, further comprising:
   a phase control system configured to cause the transducer array to emit an ultrasonic beam, the phase control system being configured to steer the ultrasonic beam along a Y-axis of the transducer array to locate a measurement angle for the transducer array where the blood vessel is located.

5. The system of claim 1, wherein the upper electrode and the lower electrode are formed of poly-silicon.

6. The system of claim 2, wherein the carrier substrate includes an insulation layer on an upper surface of the substrate, and wherein the setting electrodes are formed in the insulation layer.

7. The system of claim 6, wherein the carrier substrate is formed of silicon.

8. The system of claim 6, wherein the lower electrode is positioned in contact with the insulation layer when the transducer element is in the first tilted position and the second tilted position.

9. A method of compensating for misalignment of a transducer array with respect to a blood vessel, the method comprising:

placing the transducer array on an area of skin, the transducer array including a plurality of transducers, each of the transducers respectively including:
  a carrier substrate having an upper surface;
  a first spacer and a second spacer extending upwardly from the upper surface;
  a transducer element supported above the upper surface of the carrier substrate by the first spacer and the second spacer, and the transducer element is spaced apart from the upper surface of the substrate;
  an upper electrode positioned on an upper surface of the transducer element facing away from the carrier substrate;
  a lower electrode positioned on a lower surface of the transducer element facing toward the carrier substrate; and
  setting electrodes positioned on the upper surface of the substrate under the transducer element;

locating a first measurement angle at which the blood vessel is located by steering an ultrasonic beam emitted by the transducer array with a phase control system with the respective transducer elements in a first tilted position;

applying a bias voltage to the setting electrodes of the respective transducers to create a potential difference between the transducer element of the respective transducers and the lower electrode of the respective transducers, the potential difference causing the respective transducer elements to pivot from the first tilted position to a second tilted position;

locating a second measurement angle at which the blood vessel is located by steering the ultrasonic beam emitted by the transducer array with the phase control system; and determining a misalignment angle for the transducer array based on the first measurement angle and the second measurement angle.

10. The method of claim 9, wherein the first tilted position defines a first angle of incidence for the transducer element, and wherein the second tilted position defines a second angle of incidence for the transducer element.

11. The method of claim 9, wherein the setting electrodes include a first setting electrode and a second setting electrode, the first setting electrode being positioned under a first side portion of the transducer element, the first side portion being located on a first side of a pivot axis, the second setting electrode being positioned under a second side portion of the transducer element, and the second side portion being located on a second side of the pivot axis.

12. The method of claim 9, wherein the upper electrode and the lower electrode are formed of polysilicon.

13. The method of claim 12, wherein the carrier substrate is formed of silicon.

14. The method of claim 13, wherein the carrier substrate includes an insulation layer on an upper surface of the substrate, and wherein the setting electrodes are formed in the insulation layer.

15. The method of claim 14, wherein the lower electrode is positioned in contact with the insulation layer when the transducer element is in the first tilted position and the second tilted position.

* * * * *